(12) United States Patent
Herrmann et al.

(10) Patent No.: US 11,340,359 B2
(45) Date of Patent: May 24, 2022

(54) MULTI-LAYER RADIATION DETECTOR

(71) Applicant: KONINKLIJKE PHILIPS N.V., Eindhoven (NL)

(72) Inventors: Christoph Herrmann, Aachen (DE); Roger Steadman Booker, Aachen (DE); Jakob Wijnand Mulder, Eindhoven (NL); Matthias Simon, Aachen (DE); Jacques Jules Van Oekel, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/609,768

(22) PCT Filed: Apr. 24, 2018

(86) PCT No.: PCT/EP2018/060399
§ 371 (c)(1),
(2) Date: Oct. 31, 2019

(87) PCT Pub. No.: WO2018/202465
PCT Pub. Date: Nov. 8, 2018

(65) Prior Publication Data
US 2020/0064496 A1    Feb. 27, 2020

Related U.S. Application Data (60) Provisional application No. 62/492,328, filed on May 1, 2017.

(51) Int. Cl.
*G01T 1/20*    (2006.01)
*A61B 6/03*    (2006.01)

(52) U.S. Cl.
CPC ............ *G01T 1/2018* (2013.01); *A61B 6/032* (2013.01)

(58) Field of Classification Search
CPC .............................. G01T 1/2018; A61B 6/032
See application file for complete search history.

(56) References Cited

U.S. PATENT DOCUMENTS

| | | | | |
|---|---|---|---|---|
| 4,467,342 A | * | 8/1984 | Tower | H01L 25/0655 257/222 |
| 4,855,598 A | * | 8/1989 | Ohgoda | G01T 1/2012 250/582 |

(Continued)

FOREIGN PATENT DOCUMENTS

| | | |
|---|---|---|
| EP | 0967655 A2 | 12/1999 |
| JP | 2011227044 A | 11/2011 |

(Continued)

OTHER PUBLICATIONS

An english translation of JP 2013-253887 A, Published (2013) (Year: 2013).*

(Continued)

*Primary Examiner* — David P Porta
*Assistant Examiner* — Djura Malevic
(74) *Attorney, Agent, or Firm* — Larry Liberchuk (57) ABSTRACT

A detector includes a first detection layer ($114_1$) and a second detector layer ($114_2$). The first and second detection layers include a first and second scintillator (204, $704_1$) (216, $704_2$), a first and second active photosensing region (210, $708_1$) (220, $708_2$), a first portion (206, $726_1$) of a first substrate (208, $706_1$), and a second portion (218, $726_2$) of a second substrate (208, $706_2$). An imaging system (100) includes a radiation source (110), a radiation sensitive detector array (108) comprising a plurality of multi-layer detectors (112), and a reconstructor (118) configured to reconstruct an output of the detector array and produces an image. The detector array includes a first detection layer and a second detector layer with a first and second scintillator, a (Continued)

first and second active photosensing region, a first portion of a first substrate, and a second portion of a second substrate.

20 Claims, 6 Drawing Sheets

(56) References Cited

U.S. PATENT DOCUMENTS

| | | | | |
|---|---|---|---|---|
| 4,870,667 A * | 9/1989 | Brunnett | | G01T 1/2018 378/19 |
| 5,065,245 A * | 11/1991 | Carnall, Jr. | | H04N 1/03 348/373 |
| 5,138,167 A * | 8/1992 | Barnes | | G01T 1/2018 250/363.02 |
| 5,420,429 A * | 5/1995 | Eberhard | | B06B 1/064 250/367 |
| 5,548,123 A * | 8/1996 | Perez-Mendez | | G01T 1/2018 250/370.09 |
| 5,825,032 A * | 10/1998 | Nonaka | | H04N 5/325 250/370.09 |
| 5,834,782 A * | 11/1998 | Schick | | H04N 5/3415 250/370.11 |
| 6,005,908 A * | 12/1999 | Oppelt | | G01T 1/2985 378/11 |
| 6,175,611 B1 * | 1/2001 | Melen | | G01T 1/243 250/332 |
| 6,181,769 B1 * | 1/2001 | Hoheisel | | A61B 6/4233 378/177 |
| 6,362,480 B1 * | 3/2002 | Peter | | G01T 1/1612 250/366 |
| 6,408,110 B2 * | 6/2002 | Schulman | | H01L 27/14601 382/312 |
| 6,448,559 B1 * | 9/2002 | Saoudi | | G01T 1/1603 250/367 |
| 6,894,283 B1 * | 5/2005 | Busse | | H04N 5/3559 250/370.07 |
| 6,965,111 B2 * | 11/2005 | Endo | | G01T 1/2928 250/370.08 |
| 7,081,627 B2 * | 7/2006 | Heismann | | G01T 1/2018 250/370.09 |
| 7,154,989 B2 * | 12/2006 | Ueno | | A61B 6/032 378/19 |
| 7,239,928 B2 * | 7/2007 | Kohl | | G06Q 10/0875 700/95 |
| 7,263,165 B2 * | 8/2007 | Ghelmansarai | | A61N 5/1049 250/370.09 |
| 7,372,035 B2 * | 5/2008 | Yokoi | | G01T 1/241 250/370.08 |
| 7,435,965 B2 * | 10/2008 | Fuchs | | G01T 1/2018 250/367 |
| 7,613,274 B2 * | 11/2009 | Tkaczyk | | A61B 6/032 378/19 |
| 7,622,719 B2 * | 11/2009 | Spahn | | G01T 1/2018 250/370.11 |
| 7,638,785 B2 * | 12/2009 | Yanagita | | G21K 4/00 250/584 |
| 7,671,342 B2 * | 3/2010 | Bani-Hashemi | | G01T 1/2018 250/370.11 |
| 7,696,481 B2 * | 4/2010 | Tkaczyk | | G01T 1/2018 250/363.02 |
| 7,728,303 B2 * | 6/2010 | Mori | | H01L 31/02322 250/370.11 |
| 7,834,321 B2 * | 11/2010 | Yorkston | | G21K 4/00 250/370.09 |
| 7,869,862 B2 * | 1/2011 | Seppi | | A61B 6/405 600/431 |
| 7,893,405 B2 * | 2/2011 | Nagano | | G01T 1/2018 250/370.11 |
| 7,968,853 B2 * | 6/2011 | Altman | | G01T 1/2018 250/370.11 |
| 8,373,132 B2 * | 2/2013 | Baeumer | | H01L 27/1446 250/366 |
| 8,476,599 B2 * | 7/2013 | Perna | | G01T 1/202 250/370.11 |
| 8,513,612 B2 * | 8/2013 | Levene | | G01T 1/2018 250/370.08 |
| 8,569,707 B2 * | 10/2013 | Watanabe | | G01T 1/2002 250/369 |
| 8,729,478 B2 * | 5/2014 | Tredwell | | G01T 1/2018 250/362 |
| 9,012,857 B2 * | 4/2015 | Levene | | G01T 1/202 250/370.09 |
| 9,140,808 B2 * | 9/2015 | Ronda | | G01T 1/2006 |
| 9,182,504 B2 * | 11/2015 | Nishino | | G01T 1/2012 |
| 9,194,960 B2 * | 11/2015 | Gagnon | | G02B 6/08 |
| 9,322,938 B2 * | 4/2016 | Kammerer | | G01T 1/2985 |
| 9,535,173 B2 * | 1/2017 | Liu | | G01T 1/2018 |
| 9,702,986 B2 * | 7/2017 | Peters | | G01T 1/2018 |
| 9,780,128 B2 * | 10/2017 | Tajima | | A61B 6/585 |
| 9,784,853 B2 * | 10/2017 | Nishino | | G01T 1/202 |
| 9,846,246 B2 | 12/2017 | Jadrich | | |
| 9,972,655 B2 * | 5/2018 | Kurokawa | | H01L 27/14612 |
| 10,345,455 B2 * | 7/2019 | Ishii | | A61B 6/4233 |
| 10,459,094 B2 * | 10/2019 | Simanovsky | | G01T 1/2018 |
| 10,520,365 B2 * | 12/2019 | Favero | | G01J 5/10 |
| 10,677,938 B2 * | 6/2020 | Onishi | | G01N 23/083 |
| 10,712,454 B2 * | 7/2020 | Liu | | A61B 6/4233 |
| 10,739,473 B2 * | 8/2020 | Baturin | | A61B 6/5235 |
| 10,761,262 B2 * | 9/2020 | Byrd | | G02B 6/12004 |
| 2002/0027201 A1 * | 3/2002 | Agano | | G01V 5/0041 250/370.11 |
| 2003/0155516 A1 * | 8/2003 | Spartiotis | | G01T 1/2928 250/370.09 |
| 2003/0169847 A1 * | 9/2003 | Karellas | | A61B 6/482 378/98.3 |
| 2004/0113085 A1 * | 6/2004 | Heismann | | G01T 1/2018 250/370.09 |
| 2004/0200971 A1 * | 10/2004 | De Keyser | | G01N 23/04 250/370.09 |
| 2004/0238750 A1 * | 12/2004 | Vafi | | G01T 1/2018 250/370.11 |
| 2005/0012046 A1 * | 1/2005 | Groh | | A61B 6/5264 250/370.09 |
| 2005/0067572 A1 * | 3/2005 | Amemiya | | G01T 1/2985 250/363.05 |
| 2005/0082491 A1 * | 4/2005 | Seppi | | A61B 6/032 250/370.11 |
| 2006/0071173 A1 * | 4/2006 | Zeman | | G01T 1/249 250/370.11 |
| 2006/0081899 A1 * | 4/2006 | Fritzler | | G01T 1/242 257/291 |
| 2006/0151708 A1 * | 7/2006 | Bani-Hashemi | | G01T 1/2018 250/370.11 |
| 2007/0040125 A1 * | 2/2007 | Sato | | H01L 27/14663 250/367 |
| 2007/0051896 A1 * | 3/2007 | Okada | | H01L 31/02322 250/370.11 |
| 2007/0085016 A1 | 4/2007 | Schulz | | |
| 2007/0164223 A1 * | 7/2007 | Hennessy | | G01T 1/2018 250/361 R |
| 2007/0221858 A1 * | 9/2007 | Abenaim | | G01T 1/2018 250/370.11 |
| 2007/0263764 A1 * | 11/2007 | Mccallum | | G01T 1/2928 378/19 |
| 2008/0011960 A1 * | 1/2008 | Yorkston | | G21K 4/00 250/370.09 |
| 2008/0165921 A1 * | 7/2008 | Tkaczyk | | A61B 6/032 378/19 |
| 2008/0253507 A1 * | 10/2008 | Levene | | G01T 1/2018 378/19 |
| 2009/0095914 A1 * | 4/2009 | Goo | | G01T 1/20 250/370.09 |
| 2009/0224162 A1 * | 9/2009 | Inuiya | | G01T 1/244 250/370.09 |
| 2009/0290680 A1 * | 11/2009 | Turner | | G01T 1/247 378/62 |
| 2010/0078573 A1 * | 4/2010 | Nishino | | G01T 1/2928 250/393 |

(56) References Cited

U.S. PATENT DOCUMENTS

| | | | |
|---|---|---|---|
| 2010/0135463 A1* | 6/2010 | Kang | G01T 1/2018 378/98.9 |
| 2010/0200760 A1* | 8/2010 | Baeumer | H01L 27/14603 250/366 |
| 2011/0017918 A1* | 1/2011 | Baeumer | G01T 1/17 250/370.11 |
| 2011/0226951 A1* | 9/2011 | Kammerer | G01T 1/2985 250/336.1 |
| 2011/0303849 A1* | 12/2011 | Tredwell | G01T 1/2018 250/362 |
| 2012/0037809 A1* | 2/2012 | Levene | G01T 1/2985 250/370.08 |
| 2012/0106698 A1* | 5/2012 | Karim | A61B 6/4241 378/37 |
| 2012/0153163 A1* | 6/2012 | Levene | G01T 1/249 250/361 R |
| 2012/0205544 A1* | 8/2012 | Nakatsugawa | G01T 1/2018 250/367 |
| 2012/0250822 A1* | 10/2012 | Helm | A61B 6/587 378/62 |
| 2013/0026377 A1* | 1/2013 | Ichimura | G01T 1/20 250/367 |
| 2013/0048864 A1* | 2/2013 | Nakatsugawa | G01T 1/2018 250/366 |
| 2013/0292574 A1* | 11/2013 | Levene | G01T 1/202 250/362 |
| 2014/0054466 A1* | 2/2014 | Kurokawa | A61B 6/4208 250/362 |
| 2014/0138553 A1* | 5/2014 | Ogawa | G01T 1/17 250/393 |
| 2015/0137088 A1* | 5/2015 | Simon | H01L 27/308 257/40 |
| 2015/0181700 A1* | 6/2015 | Rogers | H01L 25/50 361/749 |
| 2016/0054454 A1* | 2/2016 | Kato | G01N 23/046 378/19 |
| 2016/0070006 A1* | 3/2016 | Konkle | H04N 5/378 250/366 |
| 2016/0187499 A1* | 6/2016 | Granfors | G01T 1/2002 250/362 |
| 2016/0204164 A1* | 7/2016 | Zhao | G01T 1/2018 250/369 |
| 2016/0274249 A1* | 9/2016 | Vogtmeier | G01T 1/2018 |
| 2019/0120977 A1* | 4/2019 | Jacobs | G01T 1/2018 |

FOREIGN PATENT DOCUMENTS

| | | | |
|---|---|---|---|
| JP | 2013253887 A * | 12/2013 | G01T 1/20 |
| JP | 2013253887 A | 12/2013 | |
| WO | WO2012080927 A2 | 6/2012 | |
| WO | WO2013176657 A1 | 11/2013 | |

OTHER PUBLICATIONS

PCT International Search Report, International application No. PCT/EP2018/060399, dated Aug. 7, 2018.

Provaznik M. et al., "A Study of the Interface of Soldered Joins of SnInAgTi Active Solder with ITO Ceramics", Acta Polytechnica, vol. 50, No. 6, 2010.

Chang S.Y. et al., "Active Soldering of ITO to Copper", Welding Research, pp. 81-s-83-2, Apr. 2006.

Ouyang J. et al., "Conducting Polymer as Transparent Electric Glue", Advanced Materials 2006, vol. 18, Issue 16, Aug. 2006, pp. 2141-2144.

* cited by examiner

MULTI-LAYER RADIATION DETECTOR

FIELD OF THE INVENTION

The following generally relates to an imaging detector and more particularly to a multi-layer detector and is described in connection with computed tomography (CT).

BACKGROUND OF THE INVENTION

A computed tomography (CT) scanner includes an X-ray tube mounted on a rotatable gantry that rotates around an examination region about a z-axis. The X-ray tube emits radiation that traverses the examination region and a subject or object positioned therein. An X-ray sensitive radiation detector array subtends an angular arc opposite the examination region from the X-ray tube, detects radiation that traverses the examination region, and generates a signal indicative thereof. A reconstructor processes the signal and reconstructs volumetric image data indicative of the examination region and the portion of the subject or object.

An example detector includes a scintillator layer optically coupled to a photodiode layer. The scintillator material produces light photons in response to absorbing X-ray photons, which light photons are then converted to electrical signals (e.g., currents) by photodiodes. Multi-energy (spectral) detectors include multiple stacked scintillator layers, each configured to absorb X-rays photons having energy in a particular energy range. For example, with a dual-layer detector a top scintillator layer (the one closest to the X-ray tube) absorbs lower energy X-rays photons and passes higher energy X-rays photons, and a bottom scintillator layer, which is below the top scintillator layer relative to the X-ray tube, absorbs the higher energy X-rays photons.

With a horizontal dual-layer detector configuration, a top photodiode array is disposed between the top and bottom scintillator layers, and a bottom photodiode array is disposed under the bottom scintillator layer. Both photodiode arrays include traces that route the generated electrical signals to readout electronics. The top photodiode array has included a back-illuminated photodiode array or a front-illuminated photodiode array. A back-illuminated photodiode charge collection layer generally is thick (e.g., >100 μm) and thus susceptible to direct conversion of X-rays within the photodiode array substrate, which, unfortunately, may degrade image quality. A front-illuminated photodiode array requires through-silicon-vias (TSVs) to route the electrical signals through the photodiode, which, unfortunately, adds cost and complexity.

SUMMARY OF THE INVENTION

Aspects described herein address the above-referenced problems and/or others.

In one aspect, a detector includes a first and second detection layer. The first and second detection layers include a first and second scintillator, a first and second active photosensing region, a first portion of a first substrate, and a second portion of a second substrate.

In another aspect, an imaging system comprises a first and second detection layer. The first and second detection layers include a first and second scintillator, a first and second active photosensing region, a first portion of a first substrate, and a second portion of a second substrate.

In another aspect, a method includes, receiving X-ray radiation with a detector array, using the detector array to produce an electrical signal indicative of the received radiation, and reconstructing an image with the electrical signals. Furthermore, the detector array comprises a first and second detection layer, a first and second scintillator, a first and second active photosensing region, a first portion of a first substrate and a second portion of a second substrate.

These and other aspects will be apparent from and elucidated with reference to an embodiment(s) described herein.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
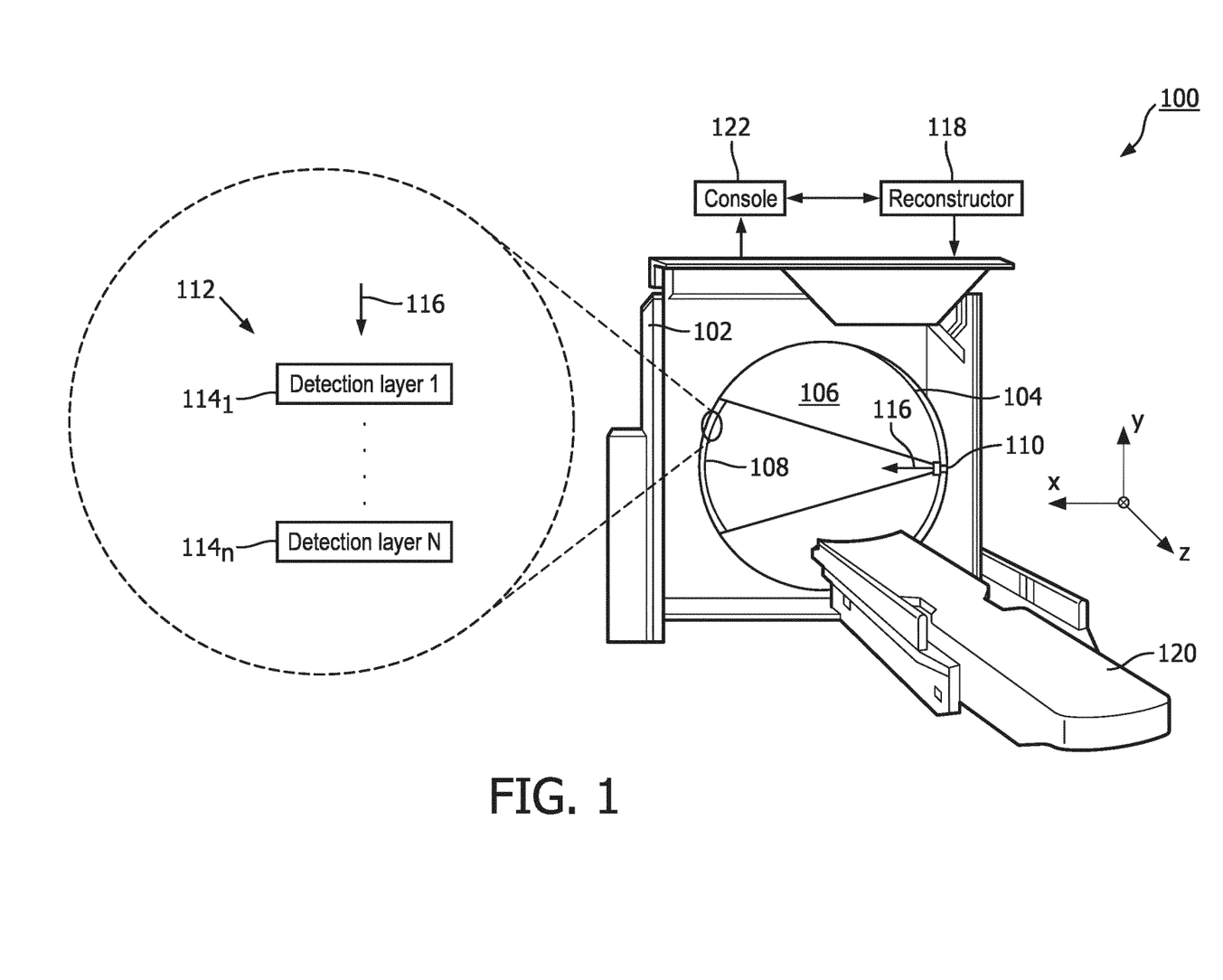
FIG. 1 diagrammatically illustrates an imaging system with a plurality of multi-layer detectors in accordance with an embodiment described herein.

FIG. 1 diagrammatically illustrates an imaging system 100 such as a computed tomography (CT) scanner, which is configured for multi-energy (spectral) imaging. The imaging system 100 includes a generally stationary gantry 102 and a rotating gantry 104, which is rotatably supported by the stationary gantry 102. The rotating gantry 104 rotates around an examination region 106 about a longitudinal or z-axis. A radiation source 110, such as an X-ray tube, is supported by and rotates with the rotating gantry 104 and emits X-ray radiation that traverses the examination region 106.

A radiation sensitive detector array 108 subtends an angular arc opposite the radiation source 110 across the examination region 106 and detects radiation traversing the examination region 106 and outputs an electrical signal (line integrals, or projection data) indicative thereof. The illustrated radiation sensitive detector array 108 includes a plurality of multi-layer detectors 112, each with a plurality of layers $114_1, \ldots, 114_N$, where N is a positive integer equal to or greater than one, collectively referred to herein as layers 114. The layers $114_1, \ldots, 114_N$ are spatially arranged with respect to each other in a horizontal configuration stacked one on top of another in a direction of a path 116 of X-ray radiation from the radiation source 110 to the detector 112.

As described in greater detail below, in one instance each of the layers 114 include a flexible (substantially) optically transparent substrate with organic photodiodes coupled thereto. Also described in greater detail below, in another instance each of the layers 114 include a front-illuminated substrate with (substantially) optically transparent electrical contacts and tracks. Some embodiments herein may reduce overall detector assembly complexity and/or cost, e.g., through eliminating any need for TSVs. Some embodiments herein are relatively thin (e.g., <20 µm), which may reduce direct conversion of X-rays in the detector layers, relative to a configuration in which the detectors 112 do not include the substrate(s) described herein. This can mitigate image quality degradation due to direct conversion of X-rays in the substrate.

A reconstructor 118 reconstructs the electrical signals and generates volumetric three-dimensional image data. In one instance, this includes employing a spectral (multi-energy) reconstruction algorithm to generate image data for a particular range of energies (e.g., high and low) or a particular energy. Additionally or alternatively, this includes employing a conventional (non-spectral) reconstruction algorithm to generate conventional (non-spectral) image data over the energy spectrum of the emitted radiation.

A subject support 120, such as a couch, supports a subject or an object in the examination region 106. A general purpose computing system serves as an operator console 122, which includes human readable output devices such as a display and/or printer and input devices such as a keyboard and/or mouse. Software resident on the console 122 allows the operator to control an operation of the imaging system 100.

Figure 2:
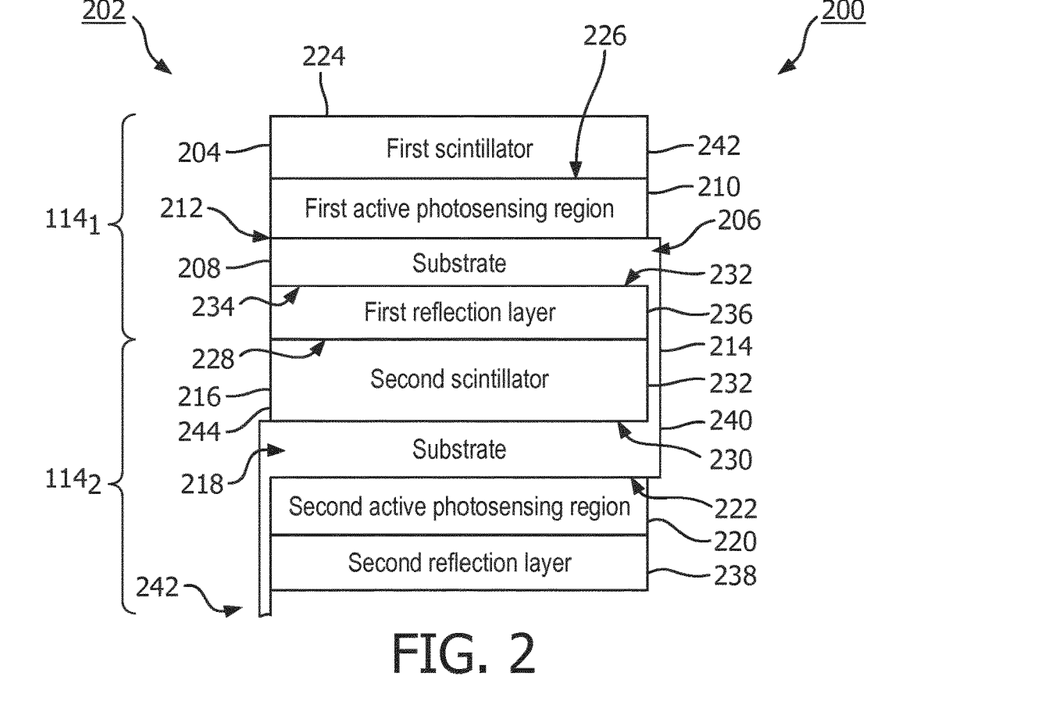
FIG. 2 diagrammatically illustrates an example of a multi-layer detector in accordance with an embodiment described herein.

FIG. 2 diagrammatically illustrates an example embodiment 200 of the multi-layer detector 112. For explanatory purposes, this embodiment is described in connection with two detection layers (N=2), i.e., a dual-layer detector 202 configuration. It is appreciated that the relative geometry (i.e., shape, size, etc.) of the components of the dual-layer detector 202 are not limiting.

The (top) detection layer $114_1$ includes a first scintillator 204, a first portion 206 of a flexible substrate 208, a first active photosensing region 210 coupled to a first region 212 on an outer or a first side 214 of the flexible substrate 208, and a first reflection layer 236 coupled to an inner or second opposing side 234 of the flexible substrate 208. The (bottom) detection layer $114_2$ includes a second scintillator 216, a second portion 218 of the same flexible substrate 208, a second active photosensing region 220 coupled to a second different region 222 on the same outer/first side 214 of the same flexible substrate 208, and a second reflection layer 238 coupled to the second active photosensing region 220. The reflection layers 236 and 238 respectively direct light photons traversing the flexible substrate 208 back towards their respective active photosensing regions 210 or 220. In some embodiments, a reflective paint or the like is on the sides of the scintillators 204 and 216 not coupled to the active photosensing regions 210 and 220.

The first scintillator 204 includes a detection surface 224 that receives X-ray radiation traversing the examination region 106 and an opposing surface 226, which is coupled to the first active photosensing region 210, e.g., via an optical coupling such as an optical adhesive or the like, through which light photons produced in the first scintillator 204 are directed to the first active photosensing region 210. The second scintillator 216 includes a detection surface 228 that receives X-ray radiation traversing the (top) detection layer $114_1$ and an opposing surface 230. The detection surface 228 is adjacent to the first reflection layer 236 and the opposing surface 230 is coupled to the inner/second side 234 of the flexible substrate 208, e.g., via an optical coupling such as an optical adhesive or the like, through which light photons produced in the second scintillator are directed to the second active photosensing region 220.

The flexible substrate 208 includes an intermediate portion 240 between the first portion 206 and the second portion 218. In this embodiment, the intermediate portion 240 does not include active photosensing region. The intermediate portion 240 includes electrical pathways (e.g., electrically conductive tracks, etc.) which route the electrical signals generated by the first active photosensing region 210. The electrical pathways extend from the first portion 206 to a portion of the substrate in electrical communication with readout electronics. The intermediate portion 240 extends out from under the first scintillator 204 traverses vertically along a side 232 of the second scintillator 216, and wraps around to the portion 218 under the second scintillator's 216 opposing surface 230. The flexible substrate 208 further includes a portion 242 which extends to the readout electronics (not shown), which may include an integrated chip (IC), application specific integrated circuit (ASIC) or the like.

In this embodiment, the first active photosensing region 210 and the second active photosensing region 220 includes organic photodiodes (OPDs). In one instance, the flexible substrate includes plastic, and the OPDs are deposited thereon via printing, chemical deposition, etc. Anode and cathode contacts and tracks (not visible) on the substrate 208 for the OPDs include a transparent metal such as Indium tin oxide (ITO), a thin sliver, Molybdenum trioxide ($MoO_3$), etc. The flexible substrate 208 is substantially transparent to the light photons. For example, in one instance the flexible substrate is at least 50% optically transparent. In another instance, flexible substrate 208 is at least 75% optically transparent. In another instance, flexible substrate 208 is at least 90% optically transparent. In other instances, flexible substrate 208 is more or less optically transparent.

Figure 3:
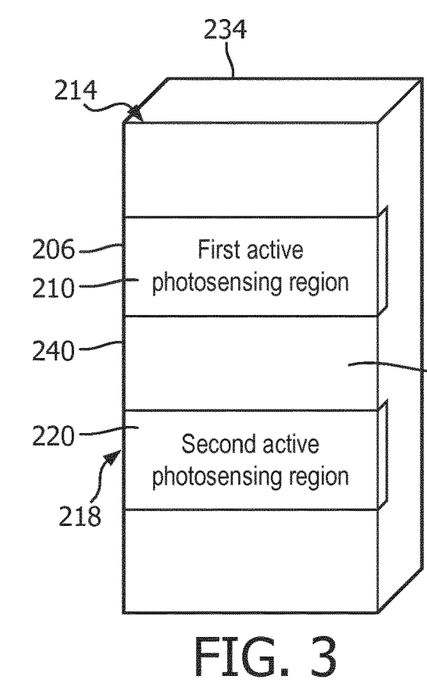
FIG. 3 diagrammatically illustrates an example of a substrate of the multi-layer detector in accordance with an embodiment described herein.
Figure 4:
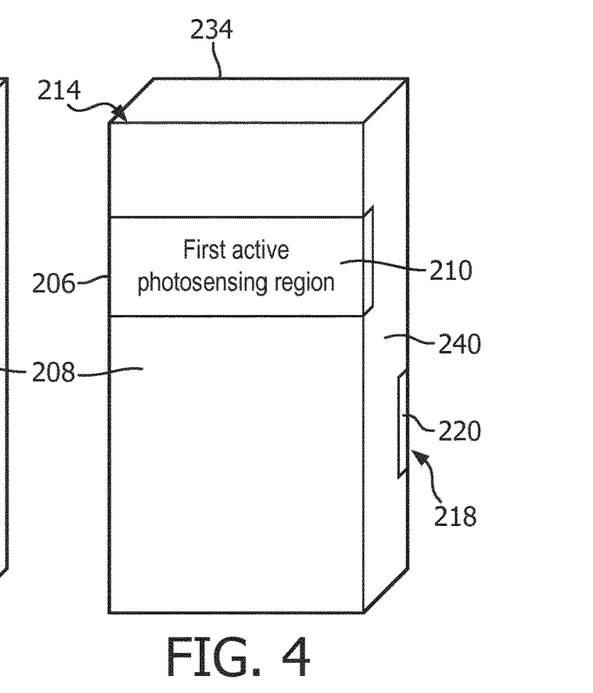
FIG. 4 diagrammatically illustrates another example of a substrate of the multi-layer detector in accordance with an embodiment described herein.

In one instance, a thickness of the combination of the active photosensing region (210 or 220) and the flexible substrate 208 is less than 20 µm thick, i.e., between 0.50 µm and 20 µm, such as, but not limited to, 6.5 µm thick, 9 µm thick, 10 µm thick, 12 µm thick, larger, smaller or in between. In the illustrated embodiment, the first active photosensing region 210 is on the outer/first side 214 of the flexible substrate 208 and the second active photosensing region 220 is on the same side 214 of the flexible substrate 208. An example of this configuration is shown in FIG. 3. In this embodiment, light generated by the second scintillator 216 traverses through the optically transparent substrate 208 and the optically transparent anode and cathode contacts and tracks and is received by the OPDs. In a variation, the first active photosensing region 210 and the second active photosensing region 220 are on opposite sides the flexible substrate 208. An example of this configuration is shown in FIG. 4.

Figure 5:
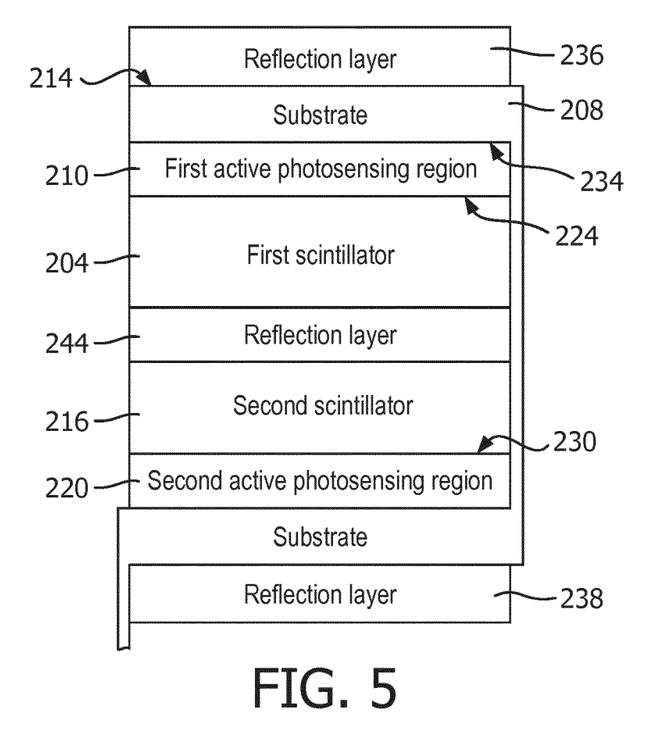
FIG. 5 diagrammatically illustrates another example of a multi-layer detector in accordance with an embodiment described herein.

FIG. 5 diagrammatically depicts a variation of the embodiment described in FIG. 2. In this variation, the first active photosensing region 210 and the second active photosensing region 220 are both coupled to the inner/second side 234 of the flexible substrate 208. The first scintillator 204 is stacked directly on top of the second scintillator 216. Furthermore, the first active photosensing region 210 is coupled to the detection surface 224 of the first scintillator 204 instead of the opposing side 226 of the first scintillator 204. Furthermore, the second active photosensing region 220 is coupled to the opposing surface 230 of the second scintillator 216.

Furthermore, the first reflection layer 236 is coupled to the outer/first side 214 of the flexible substrate 208 opposite the first active photosensing region 210, and the second reflection layer 238 is coupled to the outer/first side 214 of the flexible substrate 208 opposite the second active photosensing region 220. In FIG. 2, the first active photosensing region 210 is directly illuminated with light photons, whereas the second active photosensing region 220 is illuminated with light photons passing through the optically transparent substrate 208. In FIG. 5, both the first and the second active photosensing regions 210 and 220 are directly illuminated with light photons from respective photosensing regions 210 and 220.

Furthermore, the first and second active photosensing region 210 and 220 are not optically coupled. In one instance, a third reflection layer 244 is disposed between the first scintillator 204 and the second scintillator 216 and directs light photons traversing the first scintillator 204 back towards the active photosensing regions 210. In another instance, the substrate 208 is not optically transparent and the reflection layers 236, 238, and 244 are omitted. The remainder of the detector 112 is as described in connection with FIG. 2.

Figure 6:
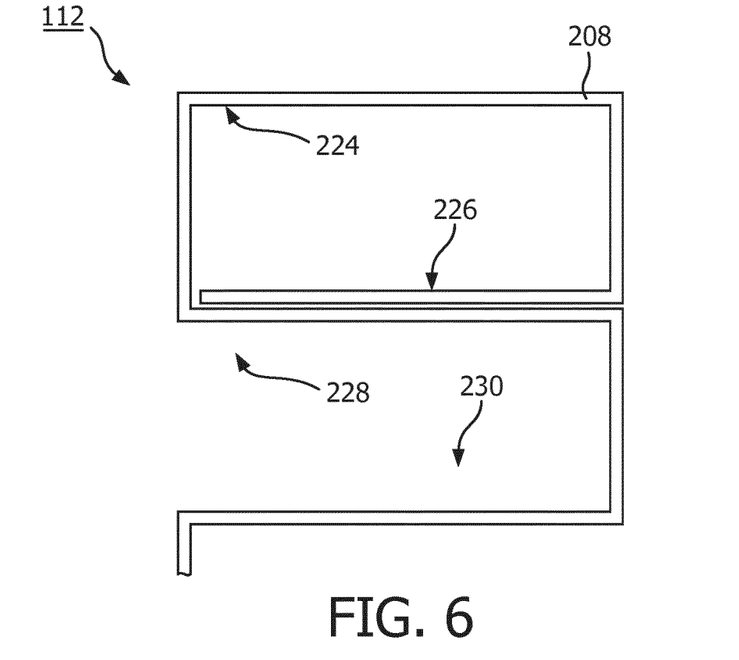
FIG. 6 diagrammatically illustrates another example of a multi-layer detector in accordance with an embodiment described herein.

FIG. 6 diagrammatically depicts another variation of the embodiment described in FIG. 2. Only the substrate 208 is shown for explanatory purposes and clarity. In this variation, the substrate 208 begins under the first scintillator 204 traversing the opposing surface 226 of the first scintillator 204, wraps around the first scintillator 204 and traverses across the detection surface 224 of the first scintillator 204, wraps around the first scintillator 204 and traverses across the detection surface 228 of the second scintillator 216, wraps around the second scintillator 216 and traverses the opposing side 230 of the second scintillator 216, and then interfaces with the readout electronics.

In one instance, the substrate 208 includes an active photosensing region coupled to only a single side of each of the scintillators 204 and 216, e.g., as shown in FIGS. 2 and 5. In another instance, the substrate 208 includes active photosensing regions coupled to two of the sides of at least one of the scintillators 204 and 216. In another instance, the substrate 208 includes active photosensing regions coupled to three of the sides of at least one of the scintillators 204 and 216. In another instance, the substrate 208 includes active photosensing regions coupled to four of the sides of at least one of the scintillators 204 and 216. The remainder of the detector 112 is as described herein at least in connection with FIG. 2.

Figure 7:
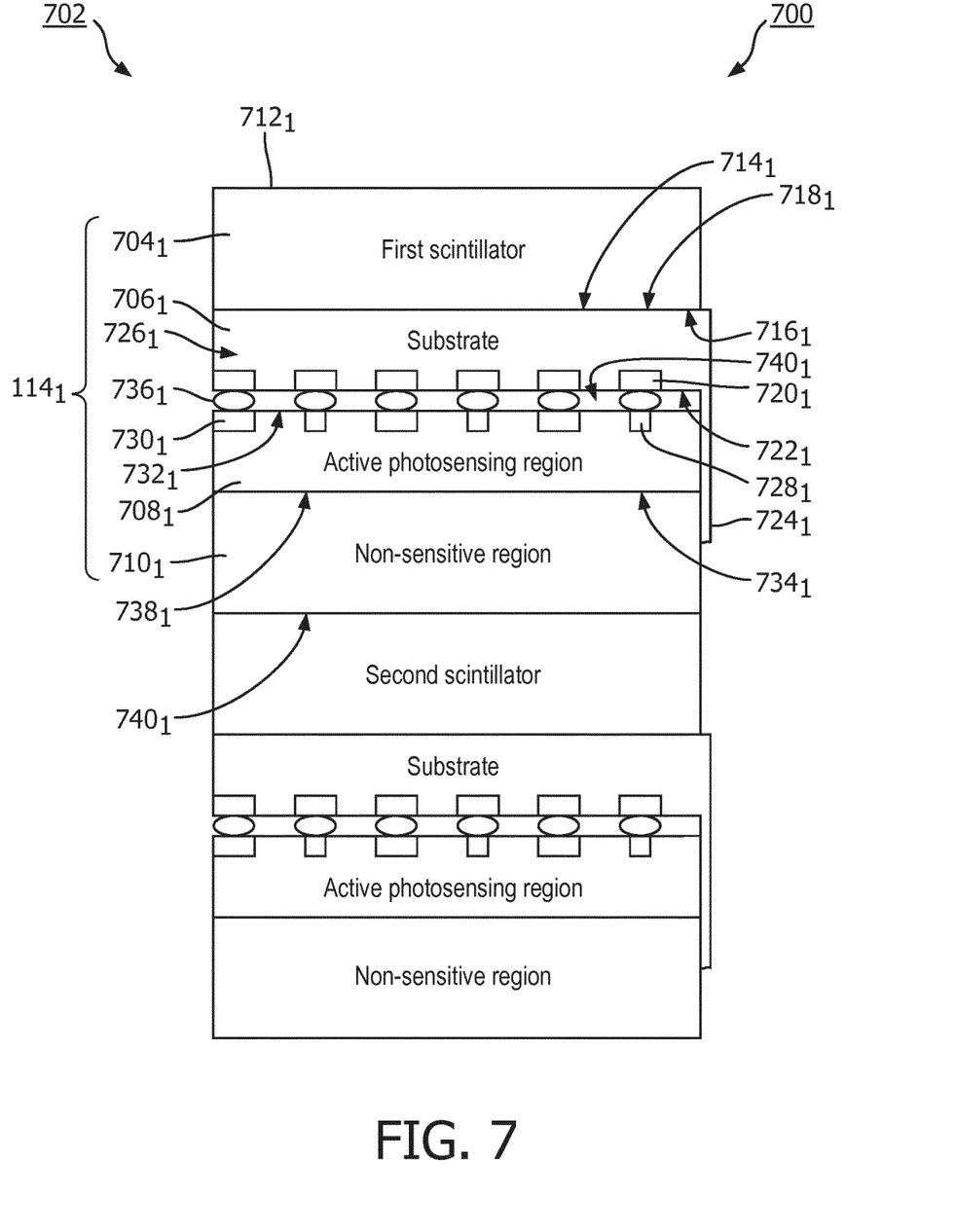
FIG. 7 diagrammatically illustrates another example of a multi-layer detector in accordance with an embodiment described herein.

FIG. 7 diagrammatically depicts an embodiment 700 of the multi-layer detector 112. Similar to FIG. 2, for explanatory purposes, this embodiment is described in connection with two detection layers (N=2), i.e., a dual-layer detector 702 configuration, and the relative geometry (i.e., shape, size, etc.) of the components of the dual-layer detector 202 are not limiting.

In this example, the two layers are substantially similar so, for the sake of brevity and clarity, only the top layer is discussed in detail below. However, it is to be understood that this discussion also applies to the bottom layer. Furthermore, wherein the elements of the first detection layer $114_1$ and the second detection layer $114_2$ are substantially the same, the element numbers, as applied to the second detection layer $114_2$, are the same as the element numbers for the first detection layer $114_1$, except denoted with a subscript 2 (i.e., $7XX_1$ in the first detection layer $114_1$ corresponds to $7XX_2$ in the second detection layer $114_2$).

The top detection layer $114_1$ includes a first scintillator $704_1$, a substrate $706_1$ with a first portion $726_1$ and a second portion $724_1$, a first active photosensing region $708_1$, and a non-sensitive region $710_1$. The first scintillator $704_1$ includes a detection surface $712_1$ that receives X-ray radiation traversing the examination region 106 and an opposing surface $714_1$, which is coupled to a first region $716_1$ of a first/top side $718_1$ of the substrate $706_1$, e.g. via an optical coupling such as an optical adhesive or the like.

The substrate $706_1$ comprises optically transparent contacts $720_1$ and tracks (not visible), e.g. including ITO and/or other optically transparent material. The optically transparent contacts $720_1$ are located on a second/bottom side $722_1$ of the substrate $706_1$. The first portion $726_1$ of the substrate $706_1$ is disposed between the first scintillator $704_1$ and the first active photosensing region $708_1$. The second portion $724_1$, which extends out past the non-sensitive region $710_1$, routes signals generated by the first active photosensing region $708_1$ from the first portion $726_1$ to the readout electronics.

The first active photosensing region $708_1$ comprises optically transparent anodes $728_1$ and cathodes $730_1$, e.g., including ITO and/or other optically transparent material, a first/top surface $732_1$, and second/bottom surface $734_1$. The anodes $728_1$ and cathodes $730_1$ are disposed on the first/top surface $732_1$ of the first active photosensing region $708_1$. The anodes $728_1$ and cathodes $730_1$ are electrically coupled to the optically transparent contacts $720_1$ of the substrate $706_1$ via optically transparent and conductive adhesive elements $736_1$ such as beads of an optically transparent and conductive glue or the like.

In one instance, the contacts $720_1$ and the anodes $728_1$ and the cathodes $730_1$ are coupled using Poly(3,4-ethylenedioxythiopene):poly(styrene sulfonate) (PEDOT:PSS) and a D-sorbitol layer that is less than 20 nanometer (nm) thick, e.g., 10 nm thick. In one instance, the conductivity (determined with a four-point measurement) was 100 $Scm^{-1}$ (Siemens per centimeter), resulting in a resistance of 33 milliohm (mOhm) for a 30 μm thick adhesive of 300 μm×300 μm cross section. PEDOT:PSS contains carbon (C), hydrogen (H), oxygen (O) and sulfur (S) (Z=16). In contrast, solders with higher Z materials such as those including indium tin (InSn) (Z=49 and 50) and Pb (Z=82) absorb more X-rays. In one embodiment, the first active photosensing region $708_1$ includes silicon (Si, Z=14).

In the illustrated embodiment, regions between the optically transparent and conductive adhesive elements $736_1$ include an optically transparent non-conductive underfill $740_1$. In another embodiment, the underfill $740_1$ is omitted. The second/bottom surface $734_1$ of the first active photosensing region $708_1$ is coupled to a first/top surface $738_1$ of the non-sensitive region $710_1$. In this embodiment, the first active photosensing region $708_1$ and the non-sensitive region $710_1$ is part of a front-illuminated photodiode. In the illustrated embodiment, a combination of the first active photosensing region $708_1$ and the non-sensitive region $710_1$ has a thickness that is less than 20 μm thick, e.g. between 0.50 and 20 μm, such as on an order of 7.5 μm thick, 9.5 μm thick, 10 μm thick, 11 μm thick, smaller, larger, or in between.

Figure 8:
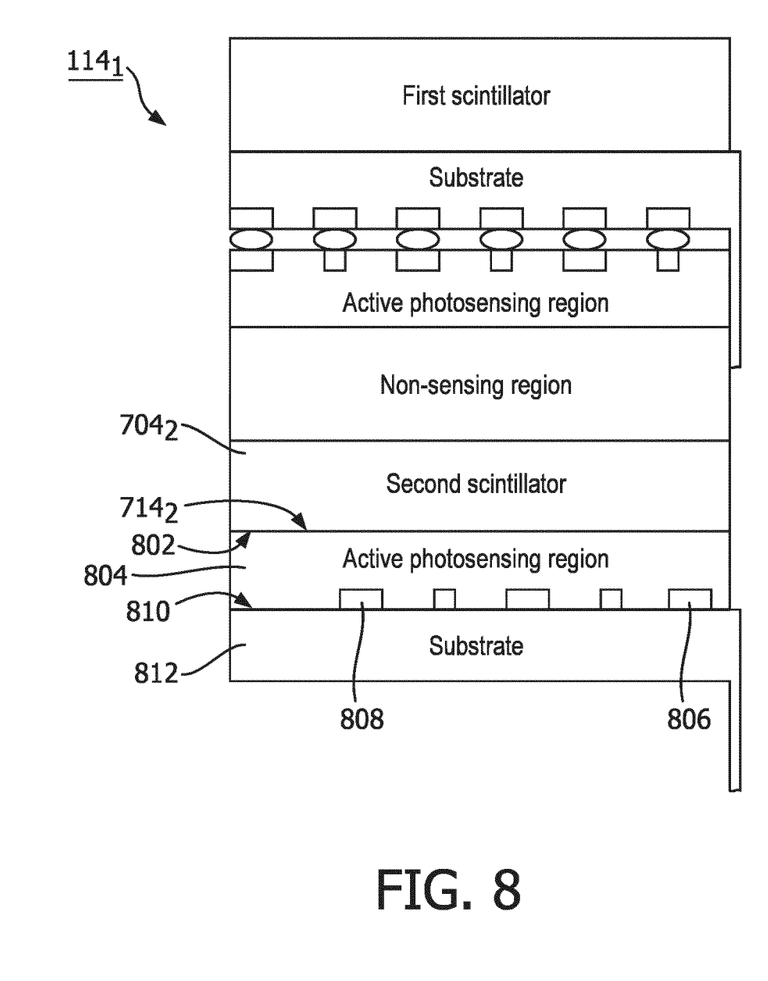
FIG. 8 diagrammatically illustrates another example of a multi-layer detector in accordance with an embodiment described herein.

FIG. 8 diagrammatically depicts a variation of the embodiment described in FIG. 7. The top detector layer $114_1$ in FIG. 8 is the same as the top detector layer $114_1$ as described in FIG. 7. In this embodiment, an opposing surface $714_2$ of a second scintillator $704_2$ is coupled to a first/top side 802 of a second active photosensing region 804. The second active photosensing region 804 comprises anodes 806 and cathodes 808 disposed on a second/bottom surface 810 of the second active photosensing region 804. The anodes 806 and cathodes 808 are electrically coupled to a substrate 812. Furthermore, the second photosensing region 804 is a back illuminated photosensing region. In this instance, the substrate 812 is not optically transparent.

Figure 9:
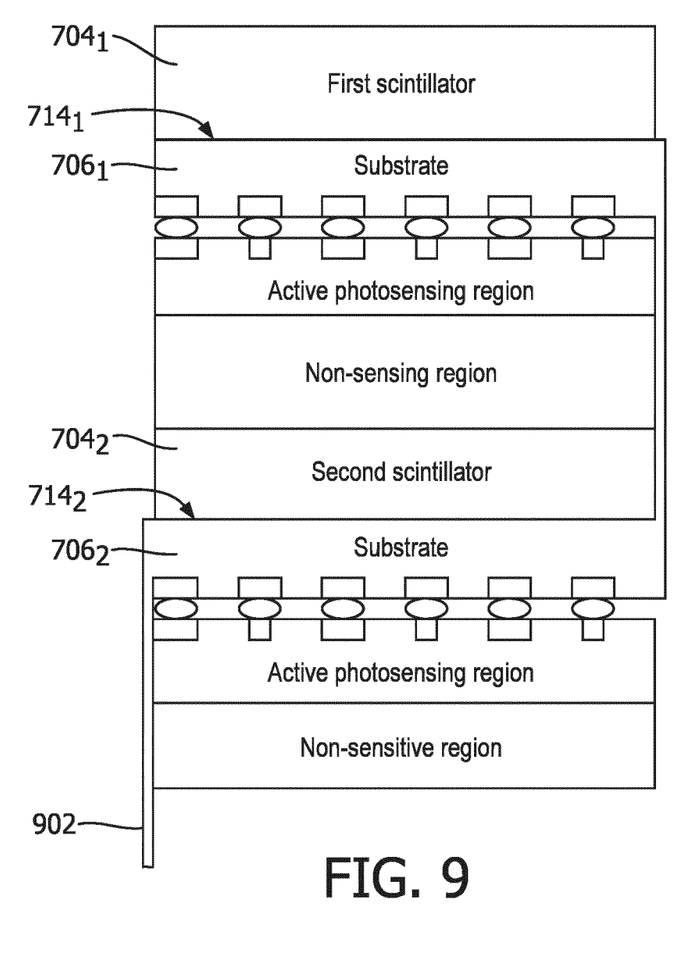
FIG. 9 diagrammatically illustrates another example of a multi-layer detector in accordance with an embodiment described herein.

FIG. 9 diagrammatically depicts another variation of the embodiment described in FIG. 7. In this variation, the substrate $706_1$ and substrate $706_2$ are sub-portions of a same substrate 902. The substrate $706_1$ begins under the first scintillator $704_1$ traversing the opposing surface $714_1$ of the first scintillator $704_1$, and wraps around the second scintillator $704_2$ to the substrate $706_2$. The substrate $706_2$ traverses opposing surface $714_2$ of the second scintillator $704_2$ and interfaces with readout electronics.

Figure 10:
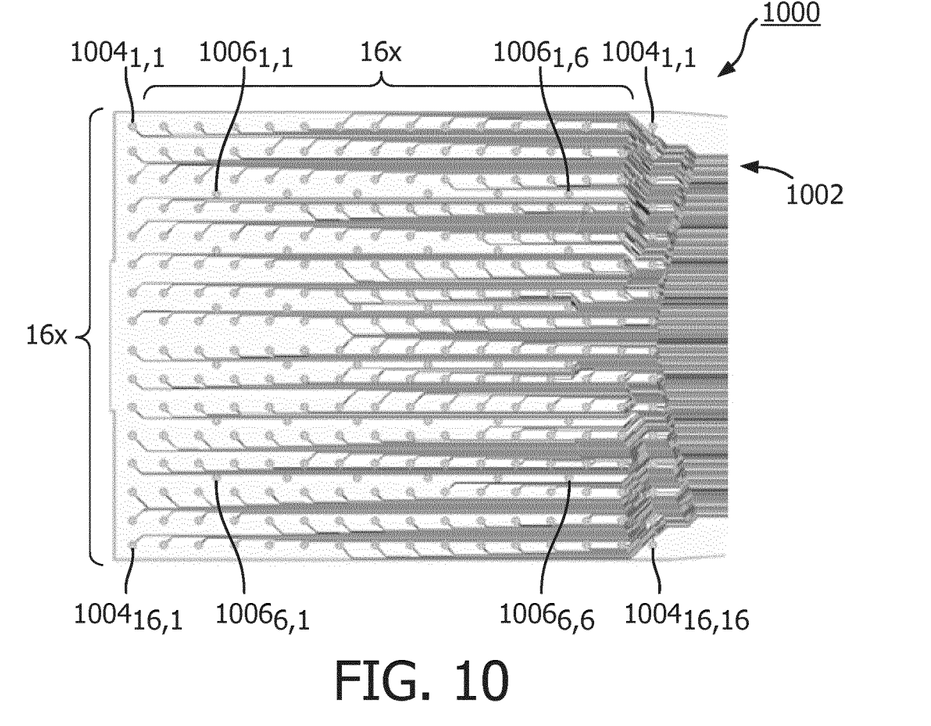
FIG. 10 diagrammatically illustrates an example of optically transparent and conductive contacts and tracks on a substrate in accordance with an embodiment described herein.

FIG. 10 diagrammatically illustrates an embodiment of a portion 1000 of the substrate 706, showing a non-limiting example of the location and routing of the optically transparent and conductive contacts 720 (FIG. 7) and tracks 1002. In this example, the portion 1000 includes a 16×16 configuration of anode contacts $1004_{1,1}, \ldots, 1004_{16,1}, \ldots 1004_{1,16}, 1004_{16,16}$, and a 6×6 configuration of cathode contacts $1006_{1,1}, \ldots, 1006_{6,1}, \ldots 1006_{1,6}, \ldots 1006_{6,6}$. A different track of the tracks 1002 respectively extends from each of the anode contacts on the substrate 706 to the readout electronics. Other, including larger and smaller, anode and/or cathode configurations are also contemplated herein.

In one instance, at least one of the optically transparent and conductive tracks 1002 are on an order of or are at least 50 μm wide, e.g. between 1.0 and 50 μm, such as 15 μm, 25 μm, 30 μm, smaller, larger, or in between. Neighboring optically transparent and conductive tracks 1002 are separated by a distance on an order of or at least 50 μm wide, e.g. between 1.0 and 50 μm, such as 15 μm, 25 μm, 30 μm, smaller, larger or in between. In one instance, the substrate 706 is a flex cable carrier such as a flexible foil with a coherent ITO layer laminated with a 100 μm thin Polyethylene terephthalate (PET) foil. An example of a suitable foil includes P86-P88 Conductive Films and Foils, products of Kitagawa GmbH, DE.

FIG. 9 illustrates a method in accordance with the embodiments described herein.

Figure 11:
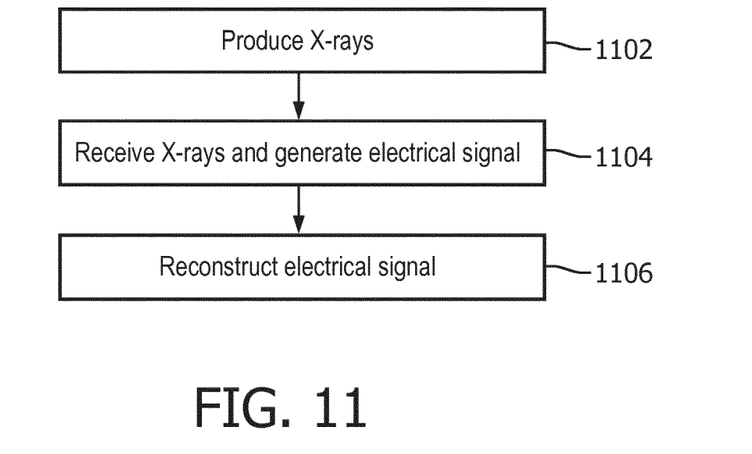
FIG. 11 illustrates a method in accordance with an embodiment described herein.

At 1102 the radiation source 110 of the imaging system 100 produces and emits X-rays.

At 1104 the detector array 108 receives X-rays traversing the examination region and generates a signal indicative thereof. The detector array 108 includes the plurality of the detectors 112, which are described herein.

At 1106 the reconstructor 118 reconstructs the electrical signals and generates volumetric three-dimensional image data. In one instance, this includes employing a spectral (multi-energy) reconstruction algorithm to generate image data for a particular range of energies or a particular energy.

The above may be implemented by way of computer readable instructions, encoded or embedded on computer readable storage medium (which excludes transitory medium), which, when executed by a computer processor (s), cause the processor(s) to carry out the described acts. Additionally or alternatively, at least one of the computer readable instructions is carried by a signal, carrier wave or other transitory medium. A computer program may be stored/distributed on a suitable medium, such as an optical storage medium or a solid-state medium supplied together with or as part of other hardware, but may also be distributed in other forms, such as via the Internet or other wired or wireless telecommunication systems.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A detector, comprising:
   a substrate comprising a first portion and a second portion;
   a first detector layer, comprising:
      a first scintillator;
      a first active photosensing region; and
   wherein the first scintillator is stacked on the first active photosensing region, which is stacked on the first portion in a direction of a path of X-ray radiation from a radiation source to the detector; and
   a second detector layer, comprising:
      a second scintillator;
      a second active photosensing region; and
   wherein the second scintillator is stacked on the second active photosensing region, which is stacked on the second portion in the direction of the path of the X-ray radiation from the radiation source to the detector;
      wherein the first detector layer is stacked on the second detector layer in the direction of the path of the X-ray radiation from the radiation source to the detector, and
      wherein the second scintillator is in contact with the substrate.

2. The detector of claim 1, wherein the substrate includes a material that is at least 75% optically transparent, the first active photosensing region includes a first set of organic photodiodes, and the second active photosensing region includes a second set of organic photodiodes.

3. The detector of claim 2, wherein a combined thickness of the first set of organic photodiodes and the substrate is in a range of 10-15 microns.

4. The detector of claim 2, wherein the substrate further comprises an outer/first side and an inner/second side, wherein the outer/first side is opposite the inner/second side, and wherein the first active photosensing region, and the second active photosensing region are coupled to the outer/first side of the substrate.

5. The detector of claim 4, wherein the substrate further comprises an intermediate portion between the first portion and the second portion, wherein the first portion is between the first scintillator and second scintillator, and the second portion is adjacent to the second scintillator.

6. The detector of claim 4, wherein the substrate further comprises an intermediate portion between the first portion and the second portion, wherein the first portion is adjacent to the first scintillator, and the second portion is adjacent to the second scintillator.

7. The detector of claim 4, wherein the first and second scintillators comprise a plurality of sides and the first active photosensing region and the second active photosensing region is adjacent to at least one of the plurality of sides.

8. The detector of claim 2, wherein the substrate further comprises an outer/first side, and an inner/second side, wherein the outer/first side is opposite the inner/second side, and wherein the first active photosensing region, and the second active photosensing region are coupled to the inner/second side of the substrate.

9. The detector of claim 2, wherein the substrate further comprises an outer/first side, and an inner/second side, wherein the outer/first side is opposite the inner/second side, and the first active photosensing region is coupled to the outer/first side, and wherein the second active photosensing region is coupled to the inner/second side of the substrate.

10. The detector of claim 2, wherein the substrate further comprises an outside/first side, and an inner/second side, wherein the outer/first side is opposite the inner/second side, and the first active photosensing region is coupled to the inner/second side, and the second active photosensing region is coupled to the outer/first side of the substrate.

11. The detector of claim 1, wherein at least the substrate comprises optically transparent and conductive contacts and tracks.

12. The detector of claim 11, wherein the first active photosensing region and the second active photosensing region comprises a first/top surface, the substrate comprises a second/bottom side, the anodes and the cathodes are disposed on the first/top surface of the substrate, the optically transparent and conductive tracks are located on the second/bottom side of the substrate, and optically transparent and conductive adhesive elements couple the anodes and the cathodes to the optically transparent and conductive tracks.

13. The detector of claim 12, wherein a region between the optically transparent and conductive adhesive elements comprises an optically transparent non-conductive underfill.

14. The detector of claim 11, wherein each of the optically transparent tracks has a width on an order of twenty-five microns.

15. The detector of claim 11, wherein neighboring optically transparent tracks are separated by a distance on an order of twenty-five microns.

16. The detector of claim 1, wherein at least the first active photosensing region comprises optically transparent anodes and optically transparent cathodes.

17. The detector of claim 1, wherein the substrate further comprises an intermediate portion between the first portion and the second portion.

18. An imaging system, comprising:
a radiation source;
a radiation sensitive detector array comprising a plurality of multi-layer detectors, wherein each of the plurality of multi-layer detectors comprises:
a substrate comprising a first portion and a second portion;
a first detector layer comprising:
a first scintillator;
a first active photosensing region; and
wherein the first scintillator is stacked on the first active photosensing region, which is stacked on the first portion in a direction of a path of X-ray radiation from a radiation source to the detector;
a second detector layer comprising:
a second scintillator;
a second active photosensing region; and
wherein the second scintillator is stacked on the second active photosensing region, which is stacked on the second portion in the direction of the path of the X-ray radiation from the radiation source to the detector;
wherein the first detector layer is stacked on the second detector layer in the direction of the path of the X-ray radiation from the radiation source to the detector, and
wherein the second scintillator is in contact with the substrate; and
a reconstructor configured to reconstruct an output of the detector array and produces an image.

19. The imaging system of claim 18, wherein the substrate includes a material that is at least 75% optically transparent, and the first active photosensing region includes a first set of organic photodiodes and the second active photosensing region includes a second set of organic photodiodes.

20. A method comprising:
receiving X-ray radiation with a detector array of an imaging system, wherein the detector array comprises a multi-layer detector, comprising:
a substrate comprising a first portion and a second portion;
a first detector layer, comprising
a first scintillator; and
a first active photosensing region;
wherein the first scintillator is stacked on the first active photosensing region, which is stacked on the first portion in a direction of a path of X-ray radiation from a radiation source to the detector; and
a second detector layer comprising:
a second scintillator; and
a second active photosensing region;
wherein the second scintillator is stacked on the second active photosensing region, which is stacked on the second portion in the direction of the path of the X-ray radiation from the radiation source to the detector,
wherein the second scintillator is in contact with the substrate;
producing an electrical signal, with the detector array, indicative of the received radiation; and
reconstructing an image with the electrical signals,
wherein the substrate includes a material that is at least 75% optically transparent, and the first active photosensing region includes a first set of organic photodiodes and the second active photosensing region includes a second set of organic photodiodes, or wherein the substrate comprises optically transparent contacts and tracks, and the optically transparent contacts are electrically coupled to optically transparent anodes and cathodes of the first and second active photosensing regions through optically transparent and conductive elements.

* * * * *